United States Patent [19]

Fischer

[11] Patent Number: Plant 7,675

[45] Date of Patent: Oct. 15, 1991

[54] AFRICAN VIOLET PLANT NAMED REGGI

[76] Inventor: Arnold Fischer, Kahlendamm 22, 3000 Hannover 51, Fed. Rep. of Germany

[21] Appl. No.: 828,092

[22] Filed: May 24, 1990

[51] Int. Cl.[5] ..... A01H 5/00
[52] U.S. Cl. ..... Plt./69
[58] Field of Search ..... Plt./69

*Primary Examiner*—James R. Feyrer

*Attorney, Agent, or Firm*—Burns, Doane, Swecker & Mathis

[57] ABSTRACT

A new and distinct cultivar of African violet named Reggi is provided. This cultivar exhibits a compact miniature rosettte growth habit, dark green pubescent foliage, and forms in abundance on upright peduncles attractive semi-double zygomorphic rotate bicolored flowers which are medium blue with white slightly undulated petal margins. The plant advantageously has a very floriferous habit with the flowering continuing for many weeks following its onset.

1 Drawing Sheet

SUMMARY OF THE INVENTION

The present invention comprises a new and distinct cultivar of African violet plant, botanically known as *Saintpaulia ionantha*, and hereinafter referred to by the cultivar name Reggi.

The new cultivar is the product of a planned breeding program and was referred to during the breeding and selection process by the designation 087-193-004. The basic objective of the breeding program was to create a new miniature bicolored African violet cultivar having an abundance of medium blue flowers possessing white slightly undulated petal margins which are borne on upright peduncles, dark green foliage, and a miniature compact growth habit.

The new cultivar originated from a cross made in this breeding program at Hannover, West Germany. The female and male parents are unknown at this time. The discovery and selection of the new cultivar occured during 1987.

Asexual reproduction of the new cultivar by leaf cuttings, as performed by me at Hannover, West Germany and at Fallbrook, Calif., U.S.A. has demonstrated that the combination of characteristics as herein disclosed for the new cultivar are firmly fixed and are retained through successive generations of asexual propagation.Reggi has not been observed under all possible environmental conditions to date. Accordingly, the phenotype may vary significantly with variations in the environment, such as temperature, light intensity, day length, etc.

The observations, measurements, and values expressed herein describe the new cultivar when grown under greenhouse conditions at Hannover, West Germany. These conditions are believed to closely approximate those commonly used in commercial practice.

The following traits have been repeatedly observed and are believed to be the basic characteristics of Reggi which in combination distinguish it as being a new and distinct African violet cultivar:

(a) forms attractive bicolored medium blue semi-double zygomorphic rotate flowers having white slightly undulated petal margins, (b) forms dark green pubescent foliage comprising oval leaves with a very slightly crenate margin having a narrow apex and a cordate base, (c) exhibits a compact miniature rosette growth habit with the flowers being held erect above the foliage on upright peduncles, and (d) exhibits a very floriferous habit with the flowers continuing to open for many weeks after the onset of flowering.

The flowers commonly exhibit a diameter of approximately 3 to 3.5 cm. When started as 6 to 8 leaf-stage plantlets, Reggi commonly finishes in 8 to 10 weeks when grown in 5 to 6 cm. pots depending upon the growing conditions encountered.

Since the new cultivar is considered to be unique, it is not meaningful to compare its characteristics to those of any previously known African violet variety.

BRIEF DESCRIPTION OF THE PHOTOGRAPHS

The accompanying photographs show as nearly true as it is reasonably possible to make the same, in color illustrations of this character, typical specimens of the plant and flowers of the new cultivar. The plants of the new variety were grown in a greenhouse at Hannover, West Germany.

FIG. 1 illustrates a typical specimen of the overall plant of the new cultivar wherein the compact growth habit, foliage and blossoms are shown, and FIG. 2 illustrates from above at the right four typical flowers of the new cultivar, and at the left a portion of a page from the R.H.S. Colour Chart of The Royal Horticultural Society, London, for comparative purposes.

DETAILED DESCRIPTION

Figure 1:
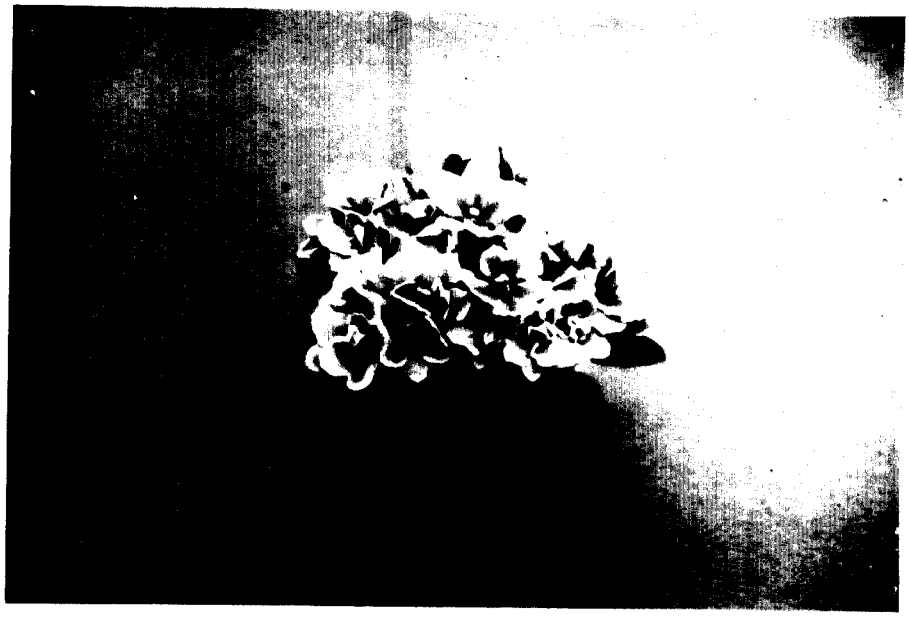
Figure 2:
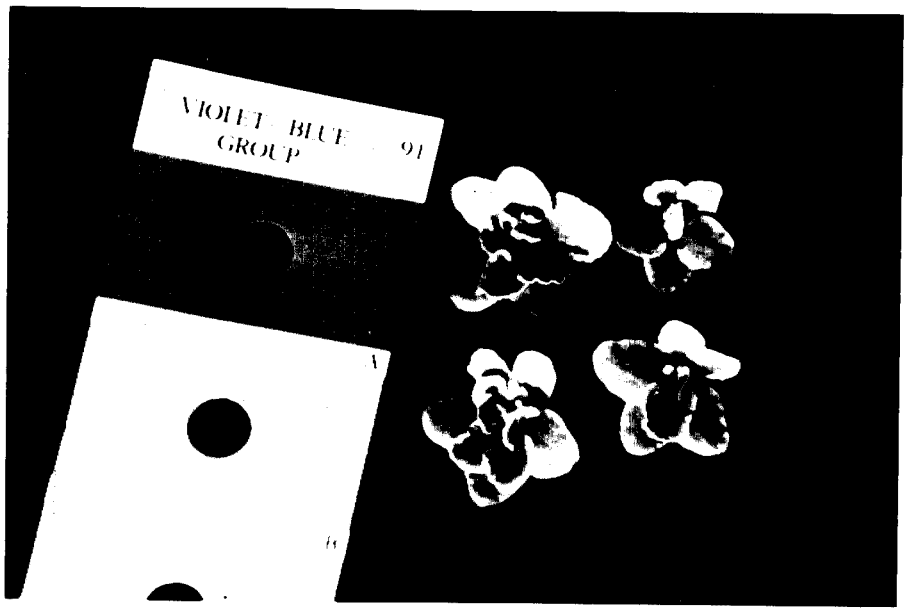

The chart used in the identification of the colors described hereafter is that of The Royal Horticultural Society (R.H.S. Colour Chart) except where general color terms of ordinary dictionary significance are expressed. The color values were taken under natural daylight conditions at 2 p.m. at Hannover, West Germany.

Botanical classification: *Saintpaulia ionantha*, Ramat., cv. Reggi.

Parentage: Unknown.

Propagation: The new cultivar holds its distinguishing characteristics through successive propagations by leaf cuttings.

Plant: Commonly approximately 3.5 to 4.5 cm. tall when grown in pots, and approximately 12 to 13 cm. in diameter when fully grown. The growth rate of plant is vigorous and the general shape of the fully grown plant is miniature compact and rosette.

Leaves:

*Quantity.*—Abundant.

*Shape.*—Oval shaped with a very slightly crenate margin, having a narrow apex and a cordate base.

*Size.*—Approximately 3 cm. in length on average-×approximately 2.5 cm. in width on average.

*Texture.*—Pubescent and glossy.

*Ribs and veins.*—Pinnate.

*Color — upper surface.*—Green Group 139A.

*Color — under surface.*—Greyed-Purple Group 187D.

*Petioles*—Greyed-Purple Group 185A.

Flowers:

*Buds.*—Size: Approximately 0.5×0.5 cm. Shape: Round. Rate of opening: Normal

*Sepals.*—Shape: 5 in number, lanceolate. Color: Greyed-Purple Group 185A.

*Phyllaries.*—Shape: 2 in number, lanceolate. Color: Brownish-green.

*Calyx.*—Size: Approximately 0.5 cm. in diameter on average. Shape: Funnel-shaped. Aspect: Pubescent.

*Peduncle.*—Length: Approximately 2.5 to 3.5 cm. on average. Character: Erect, rigid. Color: Greyed-Purple Group 185A.

Individual Flowers:

*Number of petals.*—Semi-double, commonly 5 at the outer layer and 3 to 5 at the inner layer.

*Size.*—A diameter of approximately 3 to 3.5 cm. and a depth of approximately 1 cm. commonly are exhibited.

*Shape.*—Semi-double zygomorphic rotate.

*Color — upper surface.* —Bicolored, Violet-Purple Group 91A with a margin of White Group 155A.

*Color — under surface.*—Violet-Purple Group 92C. The flower coloration can vary somewhat due to the amount of light, fertilizer, temperature and other growing conditions.

*Bearing.*—Cymose clusters on upright peduncles.

*Flowering habit.*—Flowers profusely and intermittently throughout the year with blooms commonly lasting approximately 3 to 4 weeks after which petals dry up but do not drop; finishes in approximately 8 to 10 weeks when a 6 to 8 leaf-stage plantlet is grown in a 5 to 6 cm. pot.

Reproductive organs:

*Stamens.*—Borne singly on one side of the ovary; 2 anthers are basifixed. Anthers: 2 in number; monodelphous arrangement; approximately 0.1×0.1 cm.; yellow. Filaments: approximately 0.3 to 0.4 cm.; bicolored, blue and yellow. Pollen color: Yellow

*Pistils.*—Number: 1 in number. Styles: Approximately 0.5 to 0.7 cm. in length. Stigma: Sticky, white. Ovaries: Hypogynous and tomentose.

Disease resistance: No African violet diseases have been observed to date.

I claim:

1. A new and distinct cultivar of African violet plant named Reggi characterized by the following combination of characteristics:

(a) forms attractive bicolored medium blue semi-double zygomorphic rotate flowers having white slightly undulated petal margins, (b) forms dark green pubescent foliage comprising oval leaves with a very slightly crenate margin having a narrow apex and a cordate base, (c) exhibits a compact miniature rosette growth habit with the flowers being held erect above the foliage on upright peduncles, and (d) exhibits a very floriferous habit with the flowers continuing to open for many weeks after the onset of flowering;

substantially as herein shown and described.

* * * * *

PRINTER'S FROM LINE

UNITED STATES PATENT AND TRADEMARK OFFICE

CERTIFICATE OF CORRECTION

PATENT NO. : Plant 7,675

DATED : October 15, 1991

INVENTOR(S) : Arnold Fischer

It is certified that error appears in the above-identified patent and that said Letters Patent is hereby corrected as shown below:

ON TITLE PAGE: item [21] should read:

[21] Appl. No.: 528,092

Signed and Sealed this

Ninth Day of February, 1993

*Attest:*

STEPHEN G. KUNIN

*Attesting Officer*

*Acting Commissioner of Patents and Trademarks*